United States Patent [19]

Schroeder, Jr. et al.

[11] Patent Number: 4,560,517

[45] Date of Patent: Dec. 24, 1985

[54] SULFONATION OF CRUDE OILS WITH GASEOUS SO₃ TO PRODUCE PETROLEUM SULFONATES

[75] Inventors: Donald E. Schroeder, Jr.; Mark A. Plummer; Carle C. Zimmerman, Jr., all of Littleton, Colo.

[73] Assignee: Marathon Oil Company, Findlay, Ohio

[21] Appl. No.: 180,250

[22] Filed: Aug. 22, 1980

Related U.S. Application Data

[63] Continuation of Ser. No. 22,668, Mar. 22, 1979, abandoned, which is a continuation-in-part of Ser. No. 430,963, Jan. 4, 1974, abandoned, which is a continuation-in-part of Ser. No. 238,084, Mar. 27, 1982, abandoned.

[51] Int. Cl.⁴ .................. C07C 139/00; C07C 143/24
[52] U.S. Cl. ......................... 260/505 R; 260/504 R; 260/513 T
[58] Field of Search ............. 260/505 R, 505 S, 513 T

[56] References Cited

U.S. PATENT DOCUMENTS

| | | | |
|---|---|---|---|
| 3,215,628 | 11/1965 | Peacock | 260/505 |
| 3,270,038 | 8/1966 | Marshall | 260/505 |
| 3,302,713 | 2/1967 | Ahearn | 260/505 |

*Primary Examiner*—Alan Siegel
*Attorney, Agent, or Firm*—Jack L. Hummel

[57] ABSTRACT

Petroleum sulfonates are obtained by continuously contacting whole crude oil or topped crude oil with gaseous sulfur trioxide (contains as a diluent sulfur dioxide and light hydrocarbon vapor) in a reaction zone operated at a temperature of 120°–250° F. and a pressure of 3–50 psia. The reaction product is then passed to a vapor-liquid separating stage where a vapor stream is separated and a portion of it is recycled back to the reaction zone; a liquid stream is separated from the separating stage and a portion of it is recycled back to the reaction zone. The remaining portion of the liquid stream is neutralized with a monovalent inorganic base to obtain the petroleum sulfonate. The petroleum sulfonates are particularly useful to recover crude oil from subterranean reservoirs.

32 Claims, 1 Drawing Figure

SULFONATION OF CRUDE OILS WITH GASEOUS SO₃ TO PRODUCE PETROLEUM SULFONATES

CROSS REFERENCES TO RELATED APPLICATIONS

This is a continuation of U.S. Ser. No. 22,668, filed Mar. 22, 1979, and titled "Sulfonation of Crude Oils with Gaseous SO$_3$ to produce Petroleum Sulfonates," now abandoned, which is a continuation-in-part of U.S. Ser. No. 430,963, filed Jan. 4, 1974 and titled "Sulfonation of Crude Oils with Gaseous SO$_3$ to produce Petroleum Sulfonates," now abandoned, which in turn is a continuation-in-part of U.S. Ser. No. 238,084, filed Mar. 27, 1972 and titled "Sulfonation of Crude Oils To Produce Petroleum Sulfonates," now abandoned.

BACKGROUND OF THE INVENTION

1. Field of the Invention

This invention relates to compositions useful for injecting into subterranean reservoirs to recover crude oil therefrom and more specifically to petroleum sulfonates obtained by reacting aromatic hydrocarbon with gaseous SO$_3$.

2. Description of the Prior Art

Petroleum sulfonates have been prepared by a variety of means, for example, sulfonated with sulfur dioxide (U.S. Pat. No. 2,999,812), sulfur dioxide and chlorine (U.S. Pat. No. 2,197,800), oleum (U.S. Pat. No. 2,845,455), and sulfur trioxide (U.S. Pat. No. 3,183,183). U.S. Pat. Nos. 3,215,628 and 2,815,370 teach the use of specific hydrocarbon fractions. Other patents of lesser interest include U.S. Pat. No. 2,174,508; 2,800,962; 3,173,864; 3,308,068, 3,244,622; and 3,418,239.

The prior art suggests that whole crude oil can be sulfonated and used in oil production. (See U.S. Pat. No. 1,822,271; 3,126,952; and 3,302,713 teaching the use of whole crude sulfonates in secondary-type oil recovery and U.S. Pat. Nos. 2,798,851; 2,953,525; and 3,198,832 teaching the use of such sulfonates in drilling muds). However, we are unaware of a teaching as to how this can be done or any commercial use of such a process. Specific teachings of which we are aware require the removal of the light and/or heavy ends and the use of only the middle cuts to obtain the petroleum sulfonates.

There are a number of reasons for fractionating crudes prior to sulfonation. Inter alia, it is difficult to obtain a marketable product from asphaltenes which tend to form tarry materials which foul reactors and sometimes form coke-like deposits. Also, the light ends are often aliphatics or light aromatics which will not produce the desired product.

We have now discovered that commercially acceptable sulfonates can be prepared from a variety of crude oils using our processes. While we were surprised to be able to prepare sulfonates in good yields and without coking or the formation of tarry products, we were pleased when we found that the sulfonates produced economic micellar systems suitable for use in oil recovery.

The upcoming "energy crisis" puts our invention in context. T. M. Geffen (Oil & Gas Journal, May 7, 1973, pp. 66–76) indicates that 55 billion barrels of additional crude can be recovered via tertiary recovery. Heretofore, tertiary recovery processes (see U.S. Pat. Nos. 3,254,714; 3,307,628; 3,504,744; 3,261,399; 3,497,006; 3,506,070, 3,354,953; 3,330,344 and 3,348,611—most using petroleum sulfonate surfactants) have all proved uneconomic because, inter alia, the cost of materials used made the processes uneconomic and the amounts of oil recovered were too small. Our process provides sulfonates at a price sufficiently low to aid substantially in the commercialization of tertiary oil recovery using secondary-type oil recovery techniques taught in the above-listed patents.

According to the present invention, a substantially continuous flow of sulfur trioxide in the gas phase is reacted with a hydrocarbon which can be either whole crude oil or topped crude oil or mixtures thereof. The contact occurs in a reaction zone fed by a substantially continuous flow of said hydrocarbon at temperatures, pressures, and other conditions as described hereinafter, and is followed by neutralization and possible extraction of unreacted hydrocarbons. The invention thus offers the substantial advantage of being able to produce valuable petroleum sulfonates from crude oils without fractionation (other than optional "topping" to remove low boiling fractions, usually paraffinic and not very reactive). The simplicity of this technique permits the use of portable sulfonation facilities which can manufacture petroleum sulfonates in the oil field. Thus, the present invention offers the opportunity to manufacture sulfonates for use in petroleum recovery by use of substantially untreated recovered petroleum with all of the attendant advantages over existing techniques which require substantial refining prior to sulfonation, use of selected fractions of petroleum in order to provide sulfonates suitable for preparation of micellar systems, and the transportation from the producing field to the refinery and then the sulfonation plant and thence to the point of use in the field.

UTILITY OF THE INVENTION

The petroleum sulfonates of the present invention are useful in a wide variety of applications, including the preparation of cleaning compositions, frothing agents for oil flotation, and other purposes to which petroleum sulfonates are conventionally put. However, the most preferred application of the products of the present invention is the preparation of micellar systems and emulsions, especially those useful for the recovery of crude oil from subterranean reservoirs. The petroleum sulfonates of the present invention can be substituted as the surfactants in the techniques taught in each of the petroleum recovery patents mentioned above under "Prior Art". In many cases, no further modifications of the formulations taught in those patents will be necessary. Where greater or lesser amounts of the sulfonates of the present invention are required, these amounts may be readily determined by routine trial preparation of micellar systems and routine evaluation of such systems, e.g., by core flooding tests.

BRIEF DESCRIPTION OF THE DRAWING

The drawing shows a preferred embodiment of the sulfonation process wherein crude oil is first dried, then contacted with sulfur trioxide and a Nash compressor is used to compress the effluent from the reaction zone. Sulfur dioxide (reaction by-product from the sulfonation reaction) and light hydrocarbon vapor (light ends from the crude oil) act as diluents for the reaction. Excess sulfur dioxide is contacted with water and ammonia to convert the sulfur dioxide to bisulfite and sulfite salts and these salts are admixed with the ammonium sulfonate. A portion of the liquid from the reactor separator is cooled and recycled back to the sulfonation reaction zone—the residue of the liquid is neutralized with an aqueous ammonium hydroxide solution to obtain a substantially neutralized sulfonate stream. This sulfonate stream is then permitted to phase separate into an unreacted oil phase and a petroleum sulfonate phase which is thereafter cooled, contacted with sufficient ammonia to obtain a pH of about 7–10 and is then filtered. The filtrate is admixed with a cosurfactant to obtain a micellar dispersion. The unreacted oil from the settler is used to extract the heavier molecular weight hydrocarbons from the light hydrocarbon vapor.

DESCRIPTION OF THE PREFERRED EMBODIMENTS

Figure 1:
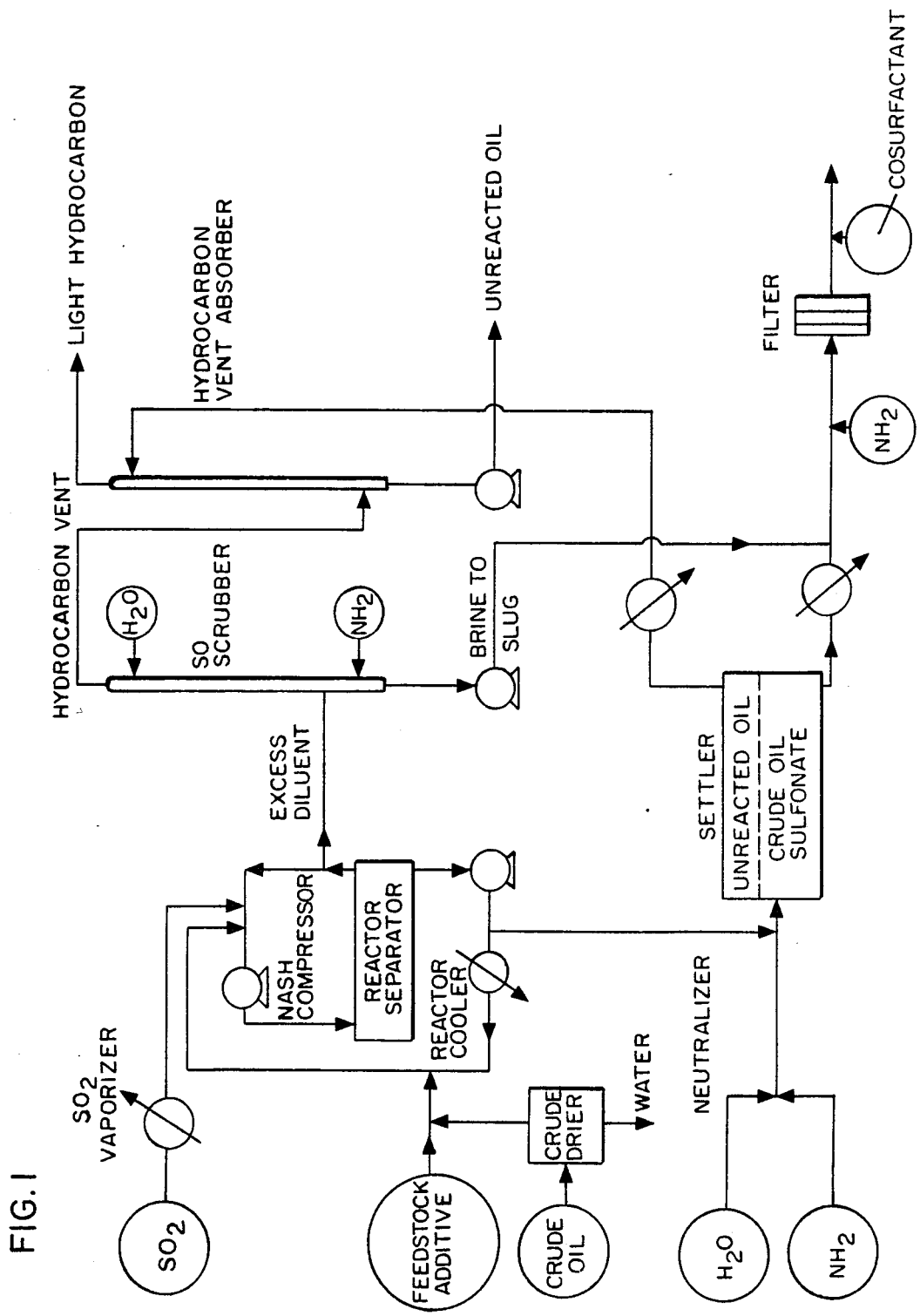

Starting Materials: Hydrocarbon Feed—It is an important aspect of the present invention that whole crude oil or topped crude is sulfonated. Previous processes have sulfonated gas oils without achieving the simplicity of the present invention. Crude oils which are particularly useful for the practice of the invention are those which are relatively high in aromatic content; but, lubricating oil base crudes (low aromatic content) are also acceptable.

The crude oil may be substituted with non-interfering substituents, e.g., $NO_3$, $Cl_2$, $SO_4$, etc., but will preferably be a hydrocarbon. Preferred crude oils are those with aromatic portions having molecular weights in the range of about 200 to about 1000, more preferably about 300 to about 800, and most preferably about 350 to about 500. The aromatic content of the crude oil is preferably about 10 to about 95, more preferably about 20 to about 80, and most preferably about 25 to about 50 weight percent aromatics as defined in American Petroleum Institute Project 60 Reports 4–7 entitled "Characterization of Heavy Ends of Petroleum". Texas crudes, Libyan crudes, Louisiana crudes, Wyoming crudes, Michigan crudes, Illinois crudes, Oklahoma crudes, Mississippi crudes, and Canadian crudes, are particularly preferred as starting materials. Especially preferred are crude oils wherein the aromatic portion has an aliphatic/aromatic proton ratio of about 3 to about 20 and more preferably about 4 to about 18.

The "aliphatic to aromatic proton ratio" used in the specification is measured on a carbon tetrachloride solution of the sample using a 60 MHz nuclear magnetic resonance spectrometer. The basic technique has been described by V. H. Luther and H. H. Oelert, Erdon and Kohle, 24, 216 (1971). All those protons which resonate with a chemical shift between 0 and 5 ppm from the tetramethylsilane internal standard are defined as aliphatic protons; those which have a chemical shift between 8.2 and 5 ppm are defined as aromatic protons. The American Petroleum Institute Project 60 Reports 4–11 entitled "Characterization of Heavy Ends of Petroleum" present data which show the polynuclear aromatic content of crude oil distillates from Wasson, Tex.; Wilmington, Calif.; Red Wash, Utah; Recluse, Wyo.; Prudhoe Bay, Alaska; Gato Ridge, Calif.; Ponca City, Okla.; and Gach Saran, Iran. Other evidence for the presence of polynuclear aromatics in crude oil is scattered throughout the petroleum literature. *The Chemistry of Petroleum Hydrocarbons,* B. T. Brooks et al, Volume I, Reinhold, 1954, discusses the concepts prevalent prior to 1954. Since that time, additional work has been done on the higher boiling crude fractions utilizing sophisticated analytical instrumentation and today there is little doubt that polynuclear aromatics are present in crude oils.

Topped crudes, e.g., those having a portion of the hydrocarbons boiling below about 600° F., and more preferably below about 350° F. and most preferably below about 200° F. removed, can be utilized in place of the whole crude oil.

The hydrocarbon feedstock is preferably dried to a water concentration less than about 1500 ppm and preferably less than 1000 ppm and more preferably less than 500 ppm. Too high of a water concentration causes the formation of sulfuric acid with the $SO_3$ and thus reduces the yield of petroleum sulfonate; it also adversely influences the phase separation of unreacted hydrocarbon from the neutralized sulfonation mixture.

$SO_3$ Diluent: The $SO_3$ stream is diluted with gas, e.g., $SO_2$ and light hydrocarbon vapor (can be refined light paraffins, light ends from the crude oil). Optionally, other gases such as air, nitrogen, natural gas, or other dry gases can be used. The ratio of the $SO_2$ and light hydrocarbon vapor to the hydrocarbon feed is 0.01 to about 10, more preferably about 0.1 to about 6, and most preferably about 1 to about 2 moles of each of the $SO_2$ and hydrocarbon vapor per 100 lbs. of the hydrocarbon feed.

The purpose of the diluent is to dilute the $SO_3$ in order to promote a more even sulfonation reaction, e.g., to reduce the amount of tri- and higher sulfonates produced. Also, the $SO_3$ diluent is necessary to reduce the partial pressure of the $SO_3$ in the reaction zone. An upper limit of about 35 psi partial pressure of the $SO_3$ is generally preferred while the desired level is down around 5 psi. If the hydrocarbon feedstock is a topped crude oil (i.e., very little light hydrocarbon vapor is present), then the concentration of $SO_2$ is preferably high to obtain a desired partial pressure of $SO_3$ in the reaction zone. While the $SO_3$ diluent will not ordinarily solubilize the sulfonates in the unreacted hydrocarbons, it has the additional advantage of lowering the viscosity of the reaction products.

Excess diluent from the vapor phase of the reactor separator is preferably scrubbed with water (can contain ions) containing a basic compound, preferably ammonia, to convert any $SO_2$ to the salts thereof, e.g. bisulfite and/or sulfite. The salts can be admixed with the petroleum sulfonate product. The $SO_2$ scrubber is preferably operated at a temperature to keep at least a majority of any hydrocarbon present as a vapor, i.e., condensing hydrocarbon in the $SO_2$ scrubber is not desired. Hydrocarbon vapor from the $SO_2$ scrubber is preferably scrubbed with unreacted oil obtained from the phase separation of the unextracted, neutralized sulfonate mixture to extract higher molecular weight fractions from this stream. Thereafter the extracted, light hydrocarbon can be flared, etc. and the unreacted oil containing extracted hydrocarbons can be used in a refinery, etc.

$SO_2$ and Light Hydrocarbon Vapor Recycle: In a vapor-liquid separating stage the effluent from the reactor zone is separated into a vapor stream and a liquid stream. At least a portion of the $SO_2$ vapor stream [comprised of $SO_2$ and light hydrocarbon vapor (contains hydrocarbons having molecular weights up to about 125 and preferably the average molecular weight is less than about 75)] is recycled back to said reaction zone.

A portion of the liquid stream from the reactor separator is cooled to reduce its temperature by about 3° to about 50° F. and preferably about 5 to about 30 and more preferably about 8° to about 15° F. Said cooled stream is recycled back to mix with the hydrocarbon stream being fed to said reaction zone.

Sulfonation Additives: To facilitate controlling the equivalent weight distribution in the product mixture obtained from the reactions of the invention, one or more sulfonation additives can be added. These additives may be used either in conjunction with or in the absence of the aforementioned diluent. Such sulfonation additives are preferably aromatic hydrocarbons, olefinic hydrocarbons, or oxygenated hydrocarbons, and preferably have molecular weights in the range of about 200° to about 1000, or more preferably about 300 to about 800, and most preferably about 350 to about 500. Specific examples of such sulfonation additives include oxo alcohol bottoms (this is an oxygenated hydrocarbon and is defined below), catalytic cycle oil (defined in U.S. Pat. No. 3,317,422, Col. 1, lines 55 through 72), Ultraformer polymer bottoms (mixtures of alkylated benzene and naphthalenes), and aromatics (such as those produced by the process of U.S. Pat. No. 3,317,422). The sulfonation additives can be used in amounts of about 0 to 20, preferably about 2 to about 15, and more preferably about 4 to about 10 pounds of sulfonation additive per 100 pounds of hydrocarbon feedstock, i.e., crude oil or topped crude oil.

The sulfonation additives can conveniently be incorporated into the hydrocarbon feedstock before it is sulfonated. Thereafter, normal sulfonation reaction procedures are followed. The sulfonation additives are generally sulfonated (or sulfated, in the case of oxygenated hydrocarbons) and exit as part of the product mixture.

The "oxo alcohol bottoms" are specifically described in the book "Higher Oxo Alcohols" by L. F. Hatch, Enjay Company, Inc., 1957. Analysis of a typical oxo alcohol bottoms is (taken from "Oxo Ether Alcohols," Industrial and Engineering Chemistry, Bartlett, Kirshenbaum and Mussig, Vol. 51, No. 3, pages 257–258).

Molecular weight[a]: 269
Oxygen, %: 11.1
Carbon, %: 75.2
Hydrogen, %: 13.7
Hydroxyl No., mg. KOH[b]: 204
Infrared spectra:
  Ether peak at 9 microns: Yes
  Alcohol peak at 9.6 microns: Yes

[a]Determined by cryoscopic method.
[b]By acetic anhydride-pyridine back-titration.

The components within the oxo alcohol bottoms can be alkoxylated, e.g., about 1–50 moles of an alkylene oxide such as ethylene oxide, propylene oxide, etc. can be used. Examples of commercially available oxo alcohol bottoms are the C-8 Oxopolymer and C-10 Oxopolymer products of Houdry Process and Chemical Co., Delaware City, Del.; Monsanto oxo alcohols, e.g., oxo alcohol 100 and heavy oxo ends, Monsanto Company, St. Louis, Mo., etc.

Sulfur Trioxide: The sulfur trioxide useful with the present invention can be of the usual commercial purity though high purity or relatively crude materials may be used in specialized circumstances where warranted by the desired products. The sulfur trioxide should be preferably substantially anhydrous and should be free from substantial quantities of impurities which would cause deleterious side reactions. About 3 to about 30, preferably about 5 to about 15, and more preferably about 8 to about 12 lbs $SO_3$ per 100 lb of hydrocarbon feedstock is useful with this invention.

If the $SO_3$ treat level is too high, tarry by-products may be obtained. In addition, inefficient oil recovery may be obtained.

Reaction Catalyst: While no catalyst will generally be employed with the present invention, known sulfonation catalysts can be employed where desired.

Reaction Temperature: In order to obtain the preferred product, the sulfonation reaction temperature should be about 120° to about 250° F., preferably about 145° to about 220° F., and more preferably about 170° to about 190° F. Temperatures lower than 120° F. may cause plugging of the reactor (due to viscous, tarry by-products, etc.) and temperatures higher than 250° F. may cause decomposition of the component(s) within the reaction product.

Reaction Pressure: Improved petroleum recovery is obtained when the pressure in the reaction zone is maintained in the range of about 3 to about 50, preferably about 9 to about 35, and more preferably about 15 to about 25 psia. At pressures greater than 50 psia, the partial pressure of the gaseous $SO_3$ is generally too high to obtain a desired product, i.e., the sulfonate is generally too hydrophilic for efficient oil recovery. Also, at high pressures, large amounts of $SO_3$ diluent may be needed to obtain a desired level of $SO_3$ partial pressure.

Contact Time: The contact time between the hydrocarbon feedstock and $SO_3$ contact time and the time the reaction mixture enters the separator will generally be within the range of about 0.01 to about 30 seconds, preferably about 0.1 to about 10 seconds and more preferably from about 0.5 to about 5 seconds. Times as short as 0.005 to about 30 seconds may be employed.

Reaction Apparatus: The preferred apparatus is a continuous flow tubular reactor having an inlet for admitting the hydrocarbon feedstock, plus any additive plus some recycle reaction products, an inlet for the $SO_3$ stream, and a vapor inlet and an outlet. Streams should be in turbulent flow within the reaction apparatus. A Nash pump (e.g., Hytor vacuum pump, Nash Engineering Co., Norwalk, Conn.) is especially useful to compress the effluent from the reaction zone and transfer the effluent to a vapor liquid separator (referred to in the drawing as the reactor separator). The compressor or pump should be sufficient to obtain a differential pressure of at least 0.01 psi and preferably at least about 0.1 to about 20 psi. Also, the differential pressure should be sufficient to cause the recycled vapor to enter the reaction zone and to become substantially dispersed in the $SO_3$ vapor stream.

The reactor is preferably made of stainless steel but any metal or non-metal having proper mechanical and corrosion-resistant properties may be utilized.

The amounts of unreacted hydrocarbon and salt contents in the final petroleum sulfonate product can be controlled by the operating conditions of the extraction process, the extraction additive to the unextracted sulfonate mix ratio and the extraction-additive composition. For example, about 0.8 to about 2.0 lbs, preferably about 1.0 to about 1.8 lbs and more preferably about 1.1 to about 1.5 lbs of aqueous alcohol solution or water can be admixed with each lb of the unextracted sulfonate mix. A preferred extraction additive composition is water containing about 50 to about 80% and more preferably about 55 to 75% by weight of ispropanol—this composition is preferred where the unextracted sulfonate mix contains about 15 weight percent water.

The mixture resulting after addition of the extraction additive will separate into either two or three phases; a raffinate phase which consists primarily of unreacted hydrocarbons, an extract phase which contains most of the petroleum sulfonate product, and possibly (depending on the particular extraction solvent used) a brine phase which contains salts and water.

The raffinate phase can be processed, e.g., by stripping, to recover any extraction additives and water from the unreacted hydrocarbon. The extract phase can be fed into a stripper to remove water and any low boiling point additive from the petroleum sulfonate product. The brine phase, if any, can be disposed of or can be further processed to recover salts, e.g., ammonium sulfate which can be utilized as fertilizer.

The petroleum sulfonate is preferably filtered to remove components which may tend to plug a subterranean reservoir. The pH of the sulfonate is preferably adjusted to about 7 to about 10 before it is filtered.

Product Specification: The desired petroleum sulfonate product has an average equivalent weight within the range of about 350 to about 525, more preferably about 375 to about 475 and most preferably about 390 to about 445. This average equivalent weight range of the petroleum sulfonate is a major quality control parameter and is directly related to the capability of the petroleum sulfonate to impart micellar characteristics to mixtures of hydrocarbon and aqueous medium. The equivalent weight of the petroleum sulfonate is defined as the sulfonate molecular weight divided by the average number of sulfonate groups per molecule. It indicates the relative amount of monosulfonation and polysulfonation, i.e., the equivalent weight becomes lower as the polysulfonation increases.

PREPARATION OF MICELLAR DISPERSION SYSTEMS

The micellar dispersion contains hydrocarbon, aqueous medium, and petroleum sulfonate. Optionally, cosurfactant and/or electrolyte can be incorporated. Examples of volume amounts include about 2% to about 90% hydrocarbon, about 5% to about 95% aqueous medium, about 4% to about 25% or more of the petroleum sulfonates (can be 50% active sulfonate), about 0.01 to about 20% cosurfactant, and about 0.001 to about 5% (weight % based on aqueous medium) of electrolyte (can be sulfite and/or bisulfites from the excess $SO_2$, sulfates, etc.). The micellar dispersions can be oil-external or water-external.

The hydrocarbon of the micellar dispersion can be crude oil, or partially refined fraction of crude oil, or refined fractions of crude oil, or synthetic hydrocarbons (including halohydrogenated hydrocarbons). The aqueous medium can be soft or hard water containing minor amounts of salts, or brackish water. The cosurfactant can be an amine, aldehyde, ketone, hydroxy-containing compound (including conventional alcohols and ethoxylated alcohols), ester, ether, mixtures thereof, etc., containing 1 to about 20 or more carbon atoms. Numerous electrolytes are useful, preferably they are inorganic acids, inorganic bases, and inorganic salts. Examples of patents which teach the use of particular components useful in micellar dispersions include those defined in the prior art as well as others known in the art.

The micellar dispersion can optionally be composed of two or more different petroleum sulfonates.

EXAMPLES

The following examples are intended to more fully illustrate the invention and are not to be considered as limiting the invention in any way. Each of the Examples utilize the apparatus shown in the drawing. The process conditions are defined in the Examples.

Each of the sulfonates produced in Examples I and II is utilized to produce a micellar dispersion having the composition given in Table A. A certain number of pore volumes (indicated under the respective example) of the resulting micellar dispersion is injected into a 6" diameter core disc (taken from the Henry reservoir, Crawford County, Ill., U.S.A.). The core disc is prepared by first saturating it with water, then flooding oil therethrough, e.g., North Crawford County's pipeline crude oil, Illinois Basin crude oil, to residual water (that is, until no more water is displaced from the core), then water flooded to residual oil (that is until no additional oil is displaced from the core) using a simulated connate water. The water-flooded core disc at this point simulates an oil field after conventional water flooding. A slug (the percent pore volume is indicated under the respective example) is then injected into the core to displace residual oil. Injection of the micellar dispersion is followed by injection of 10% PV(pore volume) of water containing 1100 ppm of Dow 700 Pusher polymer (a partially hydrolyzed, high molecular weight polyacrylamide, Dow Chemical Co., Midland, Mich.) followed by 53% PV of water containing 615 ppm of Dow 700 Pusher polymer—the water used is a simulated connate water. The "oil recovery" is calculated as the volume percent of the residual oil in place after water flooding.

EXAMPLE I

Hydrocarbon Feedstock:
Type=Illinois Basin Crude Oil (Crawford County, Ill., U.S.A.) 36° API @ 60° F.
Rate=1000 lbs/hr
$H_2O$ content—800 to 2000 ppm $H_2O$
Reaction Conditions:
Type=Back mix tubular reactor with liquid recycle for temperature control and vapor recycle for $SO_3$ dilution
Liquid Recycle ratio=4900 lbs/hr (i.e., 4.9 lbs per lb crude oil) (cooled from 181° F. to 162° F. in cooler)
Temperature=181° F.
Pressure=18.8 psia
$SO_3$ Conditions:
Rate=100 lbs/hr
Temperature of $SO_3$ Feed=268° F.
Pressure=28 psia
$SO_3$ Diluent Conditions:
Type=$SO_2$ and light hydrocarbons flashed from reactor effluent
Temperature=179° F.
Pressure=20.5 psia
Rate=270 lbs/hr (i.e., 3.27 moles/mole $SO_3$)
Composition=51.9% $SO_2$, 38.3% $C_1$-$C_7$ hydrocarbon, 9.8% $N_2$ from instrument purging, average molecular weight=about 66
$SO_3$ Partial Pressure in reaction zone=4.4 psia
Sulfonation Additive:
Type=None
Neutralization Conditions:
Reactor type=back mix flow reactor (2 stage mixer)
Temperature=162° F.

Pressure = 45 psia
NH$_3$ Rate = 26.5 lbs/hr
Water Rate = 980 lbs/hr
Neutralization pH = 5.5–6.5
Phase Separation Conditions and Output:
Temperature = 162° F.
Pressure = 13.1 psia
Time = 3.7 hours residence time in continuous settler
Unreacted Hydrocarbon Rate = 604 lb/hr
Sulfonate/Salt/Water Rate = 1455 lbs/hr
SO$_2$ Scrubber Conditions:
Water Rate = 133 lbs/hr @ 132° F.
NH$_3$ Rate = 3 lbs/hr
Brine (effluent, contains sulfite, etc.) Rate = 136 lbs/hr @ 155° F.
Brine Composition = 13.5 wt % salt reported as (NH$_4$)$_2$SO$_4$
Scrubber vent (hydrocarbon vented) = about 10 lbs/hr (No hydrocarbon vent absorber was used)
Micellar Solution (before ammonia or cosurfactant addition):
Rate = 1585 lbs/hr
Composition = 3.82 wt % —SO$_3$NH$_4$ 4.61 wt % salt reported as (NH$_4$)$_2$SO$_4$ 69.0 wt % H$_2$O. This micellar solution was diluted with water to obtain the composition given in Table A. Also, a cosurfactant was added
Sulfonate Yield = 256 lbs/hr (416 eq wt) (0.26 lbs/lb crude oil)
Oil Recovery—58.2 vol % and 54.5 vol % of residual oil after water flooding using 6" Henry Disc cores from Crawford County, Ill., using a 7% PV of micellar solution described in Table A followed by a 10% PV of 1100 ppm Dow 700 followed by 53% PV of 615 ppm Dow 700, followed by 117 ppm Dow 700 followed by Henry plant water.

EXAMPLE II

Hydrocarbon Feedstock:
Type = Illinois Basin Crude oil (Crawford County, Ill., U.S.A.) 36° API @ 60° F.
Rate = 750 lbs/hr (1070 ppm H$_2$O)
Reaction Conditions:
Type = Back mix tubular reactor with liquid recycle for temperature control and vapor recycle for SO$_3$ solution
Liquid Recycle ratio = 5600 lbs/hr (7.43 lbs per lb Crude) (cooled from 181° F. to 168° F. in cooler)
Temperature = 181° F.
Pressure = 18.0 psia
SO$_3$ Conditions:
Rate = 59.5 lbs/hr
Temperature of SO$_3$ feed = 275° F.
Pressure = 22.7 psia
Reaction Solvent Conditions:
Type = None
SO$_3$ Diluent Conditions:
Type = SO$_2$ and light hydrocarbons from reactor effluent
Temperature = 175° F.
Pressure = 20.6 psia
Rate = 360 lbs/hr (i.e., 7.3 moles/mole SO$_3$)
Composition—66 average molecular weight
SO$_3$ Partial Pressure in Reaction Zone = 2.2 psia
Sulfonation Additive:
Type = None
Neutralization Conditions:
Reactor Type = back mix flow reactor (2 stage mixer)
Temperature = 152° F.
Pressure = 47 psia
NH$_3$ Rate = 14.7 lbs/hr
Water Rate = 690 lbs/hr
Neutralization pH = 5–7
Phase Separation Conditions and Results:
Temperature = 154° F.
Pressure = 13.1 psia
Time = 12 hrs residence time
Unreacted Hydrocarbon Rate = 466 lb/hr
Sulfonate/Salt/H$_2$O Rate = 1010 lbs/hr
SO$_2$ Scrubber Conditions:
Water Rate = 85.0 lb/hr @ 128° F.
NH$_3$ Rate = 2.0 lbs/hr
Brine Rate = 87.2 lbs/hr @ 128° F.
Brine Composition = 14.82 wt % salt reported as (NH$_4$)$_2$SO$_4$
Hydrocarbon vented from scrubber = about 7 lbs/hr (No hydrocarbon vent absorber was used)
Micellar Solution (before ammonia or cosurfactant addition):
Rate = 1097 lbs/hr
Composition = 3.38 wt % —SO$_3$NH$_4$ 4.21 wt % salt reported as (NH$_4$)$_2$SO$_4$ 68.1 wt % H$_2$O.
((NH$_4$)$_2$SO$_4$ was added to the sulfonate/salt/water solution instead of the brine to keep the —SO$_3$NH$_4$ concentration at 3.38 wt %).
Sulfonate Yield = 147 lbs/hr (416 average eq et) 0.20 lbs/lb crude oil
Oil Recovery = 7.74% PV recovers 70.5 vol % and 70.3 vol % in two separate runs, and 7% PV recovers 52.3 vol % in a third run. The same polymer used in Example I is used in each of these floods.

TABLE A
MICELLAR DISPERSION COMPOSITIONS

| Sulfonate Product-in example No. | Weight % —SO$_3$NH$_4$ | Salt | Cosurfactant Type | wt % | Water | |
|---|---|---|---|---|---|---|
| I | 3.5 | 4.4 | primary amyl alcohol | 1.0 | 71.7 | Balance is the organic portion of the sulfonates plus crude oil. |
| II | 3.4 | 4.2 | primary amyl alcohol | 1.0 | 68.1 | |

MODIFICATIONS OF THE INVENTION

It should be understood that the invention is capable of a variety of modifications and variations which will be made apparant to those skilled in the art by a reading of the specification and which are to be included within the spirit of the claims appended hereto.

We claim:
1. A process for the preparation of petroleum sulfonate suitable for use with mixtures of hydrocarbon and water in secondary-type recovery of petroleum, comprising in combination contacting sulfur trioxide in the gas phase with a hydrocarbon selected from the group consisting of whole crude oil, topped crude oil and mixtures thereof in a reaction zone fed by a substantially continuous flow of said hydrocarbon, said hydrocarbon being contacted in said reaction zone with a substantially continuous flow of SO$_3$ vapor stream comprising sulfur trioxide vapor, sulfur dioxide vapor and light hydrocarbon vapor, the temperature in said reaction zone being maintained at about 120° to 250° F., the pressure in said reaction zone being maintained in the range of about 3 to about 50 psia, the reaction time being from about 0.005 to about 30 seconds; wherein each hundred pounds of hydrocarbon is contacted with about 3 to about 30 pounds of sulfur trioxide, with about 0.01 to about 10 moles of sulfur dioxide and with about 0.01 to about 10 moles of light hydrocarbon vapor; thereafter compressing the effluent from said reaction zone to a pressure of at least about 0.01 pounds per square inch higher than that prevailing in said reaction zone, thereafter separating a vapor stream and a liquid stream from said effluent in a vapor-liquid separating stage, recycling at least a portion of said vapor stream back to said reaction zone and recycling a portion of said liquid back to mix with said hydrocarbon being fed to said reaction zone, and removing the remaining portion of said liquid stream to a neutralization zone where it is reacted with a monovalent inorganic base to obtain the petroleum sulfonate which has an average equivalent weight of about 350 to about 525.

2. The process of claim 1 wherein the temperature in said reaction zone is about 145° to about 220° F.

3. The process of claim 1 wherein the pressure in said reaction zone is maintained at 9 to about 35 psia.

4. The process of claim 1 wherein the contact time between the initial contacting of the hydrocarbon with the $SO_3$ vapor stream and the time the effluent enters the separation stage is about 0.01 to about 30 seconds.

5. The process of claim 1 wherein each 100 lbs. of hydrocarbon is contacted with about 5 to about 15 lbs. of sulfur trioxide.

6. The process of claim 1 wherein each 100 lbs. of hydrocarbon is contacted with about 0.1 to about 6 moles of sulfur dioxide and with about 0.1 to about 6 moles of light hydrocarbon vapor.

7. The process of claim 1 wherein the liquid stream from the effluent is cooled to a temperature of at least about 3 to about 50° F. below the temperature of the effluent.

8. The process of claim 1 wherein a portion of the vapor stream from the vapor-liquid separating stage is contacted with sufficient amounts of a basic, aqueous solution to convert any sulfur dioxide that may be present in the vapor stream to a salt and thereafter combining the reaction product of this stream with the petroleum sulfonate.

9. The process of claim 1 wherein the petroleum sulfonate is contacted with sufficient amounts of a basic material to obtain a pH of about 7 to about 10 and wherein the resulting product is passed through a filter and the filtrate used to obtain a micellar dispersion suitable to displace crude oil from a subterranean reservoir.

10. The process of claim 1 wherein the petroleum sulfonate is permitted to phase separate into an unreacted oil phase and a petroleum sulfonate phase, the latter being the desired petroleum sulfonate product.

11. A process for the preparation of ammonium petroleum sulfonate suitable for use with mixtures of hydrocarbon and water in secondary-type recovery of petroleum, comprising in combination contacting sulfur trioxide in the gas phase with a hydrocarbon selected from the group consisting of whole crude oil, topped crude oil and mixtures thereof in a reaction zone fed by a substantially continuous flow of said hydrocarbon, said hydrocarbon being contacted in said reaction zone with a substantially continuous flow of sulfur trioxide vapor stream comprising sulfur trioxide vapor, sulfur dioxide vapor and light hydrocarbon vapor, the temperature in said reaction zone being maintained at about 145° to about 220° F., the pressure in said reaction zone being maintained in the range of about 9 to about 35 psia; wherein each 100 lbs. of hydrocarbon is contacted with about 5 to about 15 lbs. of sulfur trioxide, with about 0.1 to about 6 moles of sulfur dioxide and with about 0.1 to about 6 moles of light hydrocarbon vapor; thereafter compressing the effluent from said reaction zone to a pressure of about 0.1 to about 20 lbs. per square inch higher than the prevailing pressure in said reaction zone; thereafter separating a vapor stream and a liquid stream from said effluent in a vapor-liquid separating stage, recycling a portion of said vapor stream back to said reaction zone, cooling a portion of said liquid stream to reduce its temperature to 3° to about 50° F. and recycling this cooled liquid stream back to and mixing it with said hydrocarbon being fed to said reaction zone, and transferring the remaining portion of said liquid stream to a neutralization zone where it is reacted with aqueous ammonium hydroxide to obtain the ammonium petroleum sulfonate which has an average equivalent weight of about 350 to about 525.

12. The process of claim 11 wherein the temperature in said reaction zone is maintained at about 170° to about 190° F.

13. The process of claim 11 wherein the pressure in said reaction zone is maintained at about 15 to about 25 psia.

14. The process of claim 11 wherein the contact time from the time the hydrocarbon comes in contact with the sulfur trioxide vapor stream until the time the effluent enters the vapor-liquid separating stage is about 0.1 to about 10 seconds.

15. The process of claim 11 wherein each 100 lbs of hydrocarbon is contacted with about 8 to about 12 lbs of sulfur trioxide.

16. The process of claim 11 wherein each 100 lbs of hydrocarbon is contacted with about 1 to about 2 moles of sulfur dioxide and with about 1 to about 2 moles of liquid hydrocarbon vapor.

17. The process of claim 11 wherein the portion of said liquid stream from the separation stage is cooled to reduce its temperature to about 5 to about 30° F.

18. The process of claim 11 wherein the remaining portion of the vapor stream is contacted with sufficient amounts of an aqueous ammonium hydroxide solution to convert any sulfur dioxide which may be present in the vapor stream to sulfite and/or bisulfite and thereafter combining the product of this stream with the ammonium petroleum sulfonate.

19. The process of claim 11 wherein sufficient amounts of ammonia are admixed with the ammonium petroleum sulfonate to adjust the pH of the sulfonate to about 7 to about 10 and this stream is thereafter filtered and is then admixed with cosurfactant to obtain a micellar dispersion suitable for displacing crude oil from a subterranean reservoir.

20. The process of claim 11 wherein the ammonium petroleum sulfonate is permitted to phase separated into an unreacted oil phase and an ammonium petroleum sulfonate phase, the latter being the desired product.

21. The process of claim 1 or 11 wherein the crude oil is topped at a temperature up to 200° F.

22. The process of claim 1 or 11 wherein the hydrocarbon is crude oil.

23. A process for the preparation of petroleum sulfonate suitable for use with mixtures of hydrocarbon and water in secondary-type recovery of petroleum, comprising in combination contacting sulfur trioxide in the gas phase with crude oil in a reaction zone fed by a substantially continuous flow of said hydrocarbon, said hydrocarbon being contacted in said reaction zone with a substantially continuous flow of $SO_3$ vapor stream comprising sulfur trioxide vapor, sulfur dioxide vapor and light hydrocarbon vapor, the temperature is said reaction zone being maintained at about 120° to 250° F., the pressure in said reaction zone being maintained in the range of about 3 to about 50 psia, the reaction time being from about 0.005 to about 30 seconds; wherein each hundred pounds of hydrocarbon is contacted with about 3 to about 30 pounds of sulfur trioxide, with about 0.01 to about 10 moles of sulfur dioxide and with about 0.01 to about 10 moles of light hydrocarbon vapor; thereafter compressing the effluent from said reaction zone to a pressure of at least about 0.01 pounds per square inch higher than that prevailing in said reaction zone, thereafter separating a vapor stream and a liquid stream from said effluent in a vapor-liquid separating stage, recycling at least a portion of said vapor stream back to said reaction zone and recycling a portion of said liquid back to mix with said hydrocarbon being fed to said reaction zone, and removing the remaining portion of said liquid stream to a neutralization zone where it is reacted with a monovalent inorganic base to obtain the petroleum sulfonate which has an average equivalent weight of about 350 to about 525.

24. A process for the preparation of ammonium petroleum sulfonate suitable for use with mixtures of hydrocarbon and water in secondary-type recovery of petroleum, comprising in combination contacting sulfur trioxide in the gas phase with crude oil in a reaction zone fed by a substantially continuous flow of said hydrocarbon, said hydrocarbon being contacted in said reaction zone with a substantially continuous flow of sulfur trioxide vapor stream comprising sulfur trioxide vapor, sulfur dioxide vapor and light hydrocarbon vapor, the temperature in said reaction zone being maintained at about 145° to about 220° F., the pressure in said reaction zone being maintained in the range of about 9 to about 35 psia; wherein each 100 lbs of hydrocarbon is contacted with about 5 to about 15 lbs of sulfur trioxide, with about 0.1 to about 6 moles of sulfur dioxide and with about 0.1 to about 6 moles of light hydrocarbon vapor; thereafter compressing the effluent from said reaction zone to a pressure of about 0.1 to about 20 lbs per square inch higher than the prevailing pressure in said reaction zone; thereafter separating a vapor stream and a liquid stream from said effluent in a vapor-liquid separating stage, recycling a portion of said vapor stream back to said reaction zone, cooling a portion of said liquid stream to reduce its temperature to 3° to about 50° F. and recycling this cooled liquid stream back to and mixing it with said hydrocarbon being fed to said reaction zone, and transferring the remaining portion of said liquid stream to a neutralization zone where it is reacted with aqueous ammonium hydroxide to obtain the ammonium petroleum sulfonate which has an average equivalent weight of about 350 to about 525.

25. The process of claim 23, wherein said average equivalent weight is about 390 to about 445.

26. The process of claim 24, wherein said average equivalent weight is about 375 to about 475.

27. The process of claim 24, wherein said average equivalent weight is about 390 to about 445.

28. The process of claim 1, wherein said average equivalent weight is about 375 to about 475.

29. The process of claim 1, wherein said average equivalent weight is about 390 to about 445.

30. The process of claim 11, wherein said average equivalent weight is about 375 to about 475.

31. The process of claim 11, wherein said average equivalent weight is about 390 to about 445.

32. The process of claim 23, wherein said average equivalent weight is about 375 to about 475.

* * * * *

UNITED STATES PATENT AND TRADEMARK OFFICE
CERTIFICATE OF CORRECTION

PATENT NO. : 4,560,517
DATED : December 24, 1985
INVENTOR(S) : Donald E. Schroeder, Jr. et al It is certified that error appears in the above—identified patent and that said Letters Patent are hereby corrected as shown below:

Correct Figure 1 of the Drawings as follows:

The circle in the upper lefthand corner labeled "$SO_2$" should read --$SO_3$--.

The circle with an upward diagonal arrow through it in the upper lefthand corner labeled "$SO_2$ VAPORIZER" should read --$SO_3$ VAPORIZER--.

The circle in the lower lefthand corner labeled "$NH_2$" should read --$NH_3$--.

The circle in the lower righthand corner labeled "$NH_2$" should read --$NH_3$--.

The elongated vertical rectangle in the upper middle of the figure labeled "SO SCRUBBER" should read --$SO_2$ SCRUBBER--.

The circle pointing to the same $SO_2$ SCRUBBER labeled "$NH_2$" should read --$NH_3$--.

Signed and Sealed this

Fifteenth Day of April 1986

[SEAL]

Attest:

DONALD J. QUIGG

Attesting Officer  Commissioner of Patents and Trademarks